US012491322B2

(12) United States Patent
Sonntag et al.

(10) Patent No.: US 12,491,322 B2
(45) Date of Patent: Dec. 9, 2025

(54) DELIVERY MEMBER SHIELD REMOVER ASSEMBLY

(71) Applicant: SHL MEDICAL AG, Zug (CH)

(72) Inventors: Michael Sonntag, Taipei (TW); Jared Schwartzentruber, New York, NY (US)

(73) Assignee: SHL Medical AG, Zug (CH)

(*) Notice: Subject to any disclaimer, the term of this patent is extended or adjusted under 35 U.S.C. 154(b) by 915 days.

(21) Appl. No.: 17/634,639

(22) PCT Filed: Aug. 10, 2020

(86) PCT No.: PCT/EP2020/072399

§ 371 (c)(1),
(2) Date: Feb. 11, 2022

(87) PCT Pub. No.: WO2021/043536

PCT Pub. Date: Mar. 11, 2021

(65) Prior Publication Data

US 2022/0347395 A1 Nov. 3, 2022

Related U.S. Application Data

(60) Provisional application No. 62/896,023, filed on Sep. 5, 2019.

(30) Foreign Application Priority Data

Oct. 15, 2019 (EP) .................................... 19203148

(51) Int. Cl.
*A61M 5/32* (2006.01)

(52) U.S. Cl.
CPC ................................ *A61M 5/3204* (2013.01)

(58) Field of Classification Search
CPC .. A61M 5/3204; A61M 5/3202; A61M 5/321; Y10T 29/53; Y10T 29/49815;
(Continued)

(56) References Cited

U.S. PATENT DOCUMENTS

| | | | | |
|---|---|---|---|---|
| 10,022,503 | B2 | 7/2018 | Julian et al. | |
| 2019/0255256 | A1 | 8/2019 | Holmqvist | |
| 2022/0134020 | A1 * | 5/2022 | Yan | A61M 5/3204 604/263 |

FOREIGN PATENT DOCUMENTS

| | | | | |
|---|---|---|---|---|
| EP | 2825245 | A2 * | 1/2015 | A61M 15/0021 |
| EP | 1453561 | B1 | 8/2016 | |

(Continued)

OTHER PUBLICATIONS

International Search Report and Written Opinion for Int. App. No. PCT/EP2020/072399, mailed Sep. 23, 2020.

*Primary Examiner* — Bhisma Mehta
*Assistant Examiner* — Hayden Matthew Ritchie
(74) *Attorney, Agent, or Firm* — McDonnell Boehnen Hulbert & Berghoff LLP

(57) ABSTRACT

A delivery member shield remover assembly is presented that includes a housing which extends along a longitudinal axis L and which has a proximal and a distal end; and a delivery member shield remover having a free end and a fixed end and wherein said delivery member shield remover is resiliently connected to the housing, wherein the fixed end is connected to the housing and the free end of the delivery member shield remover is configured to be positioned in a gap defined between the medicament container and the delivery member shield such that a distal movement of the movable medicament container in relation to the housing, forces the free end of the delivery member shield remover to move in a distal direction until the delivery member shield
(Continued)

remover reaches a bias threshold and forces the delivery member shield to detach from the movable medicament container.

20 Claims, 5 Drawing Sheets

(58) Field of Classification Search
CPC ......... Y10T 29/49822; Y10T 29/53443; Y10T 29/53552; Y10T 29/53596; Y10T 29/53613; Y10T 29/53635; Y10T 29/53622; Y10T 29/5363; Y10T 29/53657; Y10T 29/5367; Y10T 29/53683; Y10T 29/53796; Y10T 29/53896; Y10T 29/53991
See application file for complete search history.

(56) References Cited

FOREIGN PATENT DOCUMENTS

| | | | | |
|---|---|---|---|---|
| EP | 2825245 B1 * | 7/2018 | ........ | A61M 15/0021 |
| WO | 2014/008373 A1 | 1/2014 | | |

* cited by examiner

DELIVERY MEMBER SHIELD REMOVER ASSEMBLY

CROSS REFERENCE TO RELATED APPLICATIONS

The present application is a U.S. National Phase Application pursuant to 35 U.S.C. § 371 of International Application No. PCT/EP2020/072399 filed Aug. 10, 2020, which claims priority to U.S. Provisional Patent Application No. 62/896,023 filed Sep. 5, 2019, and European Patent Application No. 19203148.2, filed Oct. 15, 2019. The entire disclosure contents of these applications are herewith incorporated by reference into the present application.

TECHNICAL FIELD

The present disclosure relates to a delivery member shield remover assembly and in particular, relates to a delivery member shield remover assembly adapted to interact with a delivery member shield which is releasably attached to a movable medicament container.

BACKGROUND

Medicament delivery devices such as auto-injectors, pen-injectors, inhalers, on-body devices are generally known for the self-administration of a medicament by patients without formal medical training. As just one example, those patients suffering from diabetes may require repeated injections of insulin. Other patients may require regular injections of other types of medicaments, such as a growth hormone. Reusable auto-injectors are commonly used for those patients who require repeated injections.

Most of the medicament containers in the market are provided with a removable delivery member shield for covering its delivery member; such as a needle or a nozzle; to prevent contamination of the medicament and/or accidental injuries. In the case of syringes, the most common delivery member shields are rigid needle shields (RNS) or flexible needle shields (FNS). Most of the syringes covering their delivery members with a flexible shield that ensures a tight grip and a good seal of the needle; and some of them further cover with the RNS surrounding outside of the flexible shield.

Many of these RNSs or FNSs are pushed onto the neck portion of a syringe; however this tight grip entails a problem in that it is difficult to remove the RNS or the FNS from the syringe. Such problems are even more significant if users of medicament delivery devices are elderly people; children or patients with specific diseases such like rheumatoid arthritis.

WO2014/008373 disclosed a motor driven auto injector with a needle shield stripper feature that engages a rigid needle shield such that movement of the syringe away from the front end of the injector results in removal of the rigid needle shield. The needle shield stripper feature includes one or more flanges disposed along a proximally disposed edge of the rigid needle shield or the needle shield stripper feature support housing lock onto the barrel between the barrel and the rigid needle shield; so that during movement of the syringe away from the front end of the injector, the rigid needle shield is disengaged from the syringe.

However, the rigid needle shield removal mechanism in WO2014/008373 uses a stripper, such as flanges; which require the user of the device to properly place the syringe in relation to the stripper; if the user fails to properly place the syringe, then the stripper cannot be disposed along a proximally disposed edge or lock onto the barrel between the barrel and the rigid needle shield, so that the removal mechanism might not work properly, or the stripper might be damaged; the mechanism can only be arranged with a syringe which is laterally placed in relation to the stripper or the flange, and is not compatible with the device that a syringe might need to be longitudinally placed or inserted in relation to the stripper due to the risk of damage the stripper.

SUMMARY

An object of the present disclosure is to provide a more robust and reliable delivery member shield remover assembly and more particularly for an automatic medicament delivery device, which avoids the problems of the prior art.

In the present disclosure, when the term “distal” is used, this refers to the direction pointing away from the dose delivery site. When the term “distal part/end” is used, this refers to the part/end of the delivery device, or the parts/ends of the members thereof, which under use of the medicament delivery device is/are located furthest away from the dose delivery site. Correspondingly, when the term “proximal” is used, this refers to the direction pointing to the dose delivery site. When the term “proximal part/end” is used, this refers to the part/end of the delivery device, or the parts/ends of the members thereof, which under use of the medicament delivery device is/are located closest to the dose delivery site.

Further, the term “longitudinal”, “longitudinally”, “axially” or “axial”, refers to a direction extending from the proximal end to the distal end and along the device or components thereof in the direction of the longest extension of the device and/or component.

Similarly, the terms “traverse”, “transversal”, “transversally” refer to a direction generally perpendicular to the longitudinal direction.

An object of this disclosure is provide a simple and reliable way of automatically removing a delivery member shield of a medicament container and more particularly in a medicament delivery device, especially a self-administration medicament delivery device.

According to an aspect of the disclosure, the object is achieved by a robust and reliable delivery member shield remover assembly according to claim 1.

There is hence provided a delivery member shield remover assembly adapted to interact with a delivery member shield which is releasably attached to a movable medicament container; wherein the assembly comprises: a housing which extends along a longitudinal axis L and which housing has a proximal and a distal end; and a delivery member shield remover having a free end and a fixed end and wherein said delivery member shield remover is resiliently connected to the housing, wherein the fixed end is connected to the housing and the free end of the delivery member shield remover is configured to be positioned in a gap defined between the medicament container and the delivery member shield such that a distal movement of the movable medicament container in relation to the housing, forces the free end of the delivery member shield remover to move in a distal direction until the delivery member shield remover reaches a bias threshold and forces the delivery member shield to detach from the movable medicament container.

According to one embodiment, the bias threshold is depended on the friction force between the delivery member shield and a delivery member of the medicament container or the proximal end of the medicament container.

According to one embodiment, the delivery member is a needle of an injection device, an infusion device or an on-body device.

According to one embodiment, the delivery member is a nozzle of a jet injection device, an inhalation device or a nasal sprayer.

According to one embodiment, the free end of the delivery member shield remover is movable in the proximal direction when the movable medicament container is moved in the proximal direction in relation to the housing such that the free end of the delivery member shield remover interacts with the delivery member shield until the free end of the movable delivery member shield remover contacts the gap defined between the medicament container and the delivery member shield. The movement of the movable medicament container in the proximal direction in relation to the housing is achieved by a power output source such as a manual force or an automatic or semi-automatic force when the medicament container is assembled with a cover cap of a medicament delivery device or when the medicament container is placed by a user in a medicament delivery device that is configured to automatically remove the delivery member shield.

According to one embodiment, the fixed end of the delivery member shield remover is hingedly connected to the housing.

According to one embodiment, the delivery member shield remover is integral with the housing. The fixed end of the delivery member shield remover is integral with the housing and configured such that the integral connection between the fixed end of the delivery member shield and the housing comprises resilient/biasing properties that allows the delivery member shield remover to reach a bias threshold for forcing the delivery member shield to detach from the movable medicament container.

According to one embodiment, the delivery member shield remover assembly further comprises a biasing member arranged to connect the movable delivery member shield remover and the housing, and configured to bias the movable delivery member shield remover. This is possible both for the case where the delivery member shield remover is hingedly connected to the housing and for the case where the delivery member shield remover is integral with the housing.

According to one embodiment, the biasing member is a torsion, a tension spring or a compression spring. It is also possible to obtain the same result with other kind of resilient elements/members known in the art.

According to one embodiment, the delivery member shield comprises a resilient shield member or a rigid shield member or a combination thereof. Any other kind of shield members for medicament containers known in the art are also possible.

According to one embodiment, the distal movement of the movable medicament container is driven by a motor. The motor is arranged in a medicament delivery device.

According to one embodiment, the distal movement of the movable medicament container is driven by a power accumulating member. The power accumulating member is arranged in a medicament delivery device.

According to one embodiment, the power accumulating member is a spring; such like a compression spring, tension spring, a torsion spring or a leaf spring; or a gas canister. It is also possible to obtain the same result with other kind of power accumulating elements/members known in the art.

According to one embodiment, the distal movement of the movable medicament container is manually driven. The force to manually drive the medicament container is achieved by a force exerted by a user, more particularly using a hand force. The medicament container in this embodiment may be arranged in a manually driven medicament delivery device as e.g. a safety syringe or a semi-automatic medicament injector.

According to one embodiment, the manually driven distal movement of the movable medicament container is deployed through a manually rotating gear wheel set. The manually rotating gear wheel set is arranged in a medicament delivery device.

According to one embodiment, the manually driven distal movement of the movable medicament container is deployed through manually pulling on the housing or medicament container. The medicament container in this embodiment may be arranged in a manually driven medicament delivery device as e.g. a safety syringe or a semi-automatic medicament injector.

According to one embodiment, the housing is a protective cap configured to receive the delivery member shield and which is designed to be removably attached to a medicament delivery device.

According to one embodiment, the housing is defined as being the housing of a medicament delivery device.

According to one embodiment, the medicament delivery device is an injection device, an infusion device, an on-body device, an insulin pump, an inhalation device, or a nasal or an ophthalmological sprayer.

According to one embodiment, a method of removing a delivery member shield of a medicament container, comprising: providing a housing which extends along a longitudinal axis L and which has a proximal and a distal end; and a delivery member shield remover having a free end and a fixed end and wherein said delivery member shield remover is resiliently connected to the housing; placing the medicament container with the delivery member shield movably related to the delivery member shield remover; moving the medicament container bidirectionally relatively to the delivery member shield remover until the free end of the delivery member shield remover positions in a gap defined between the medicament container and the delivery member shield; moving the medicament container in the distal direction until the delivery member shield remover reaches a bias threshold and forces the delivery member shield to detach from the movable medicament container.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the disclosed concept will now be described, by way of example, with reference to the accompanying drawings, in which.

DETAILED DESCRIPTION

The disclosed concept will now be described more fully hereinafter with reference to the accompanying drawings, in which exemplifying embodiments are shown. The disclosed concept may, however, be embodied in many different forms and should not be construed as limited to the embodiments set forth herein; rather, these embodiments are provided by way of example so that this disclosure will be thorough and complete, and will fully convey the scope of the disclosed concept to those skilled in the art. Like numbers refer to like elements throughout the description.

Figure 1:
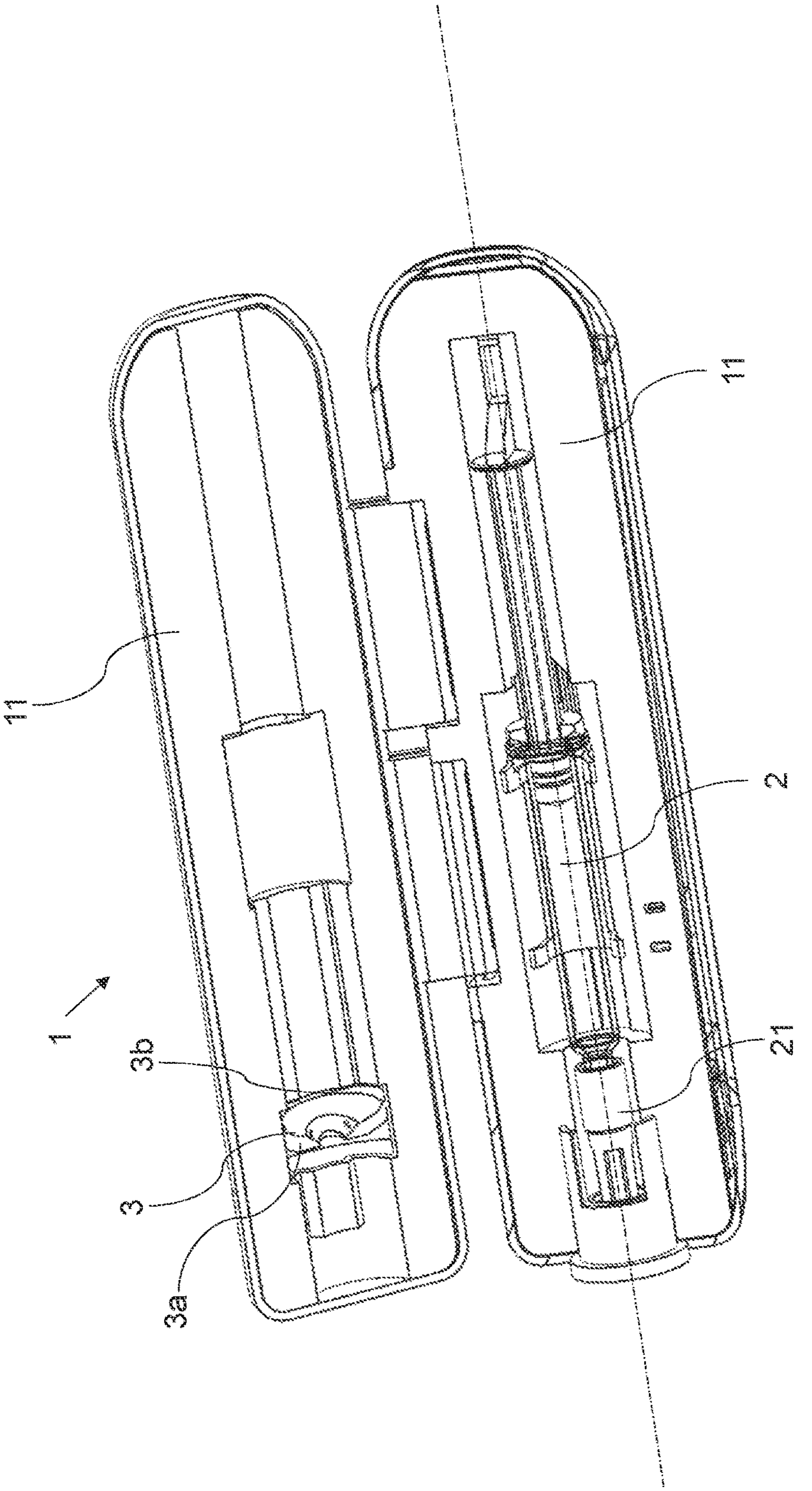
FIG. 1 displays a delivery member shield remover assembly arranged with a medicament delivery device.
Figure 6:
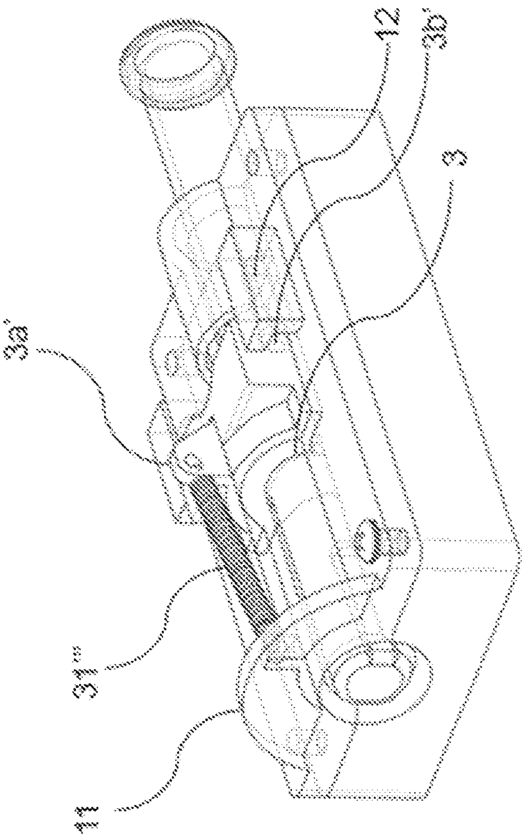
Figure 5:
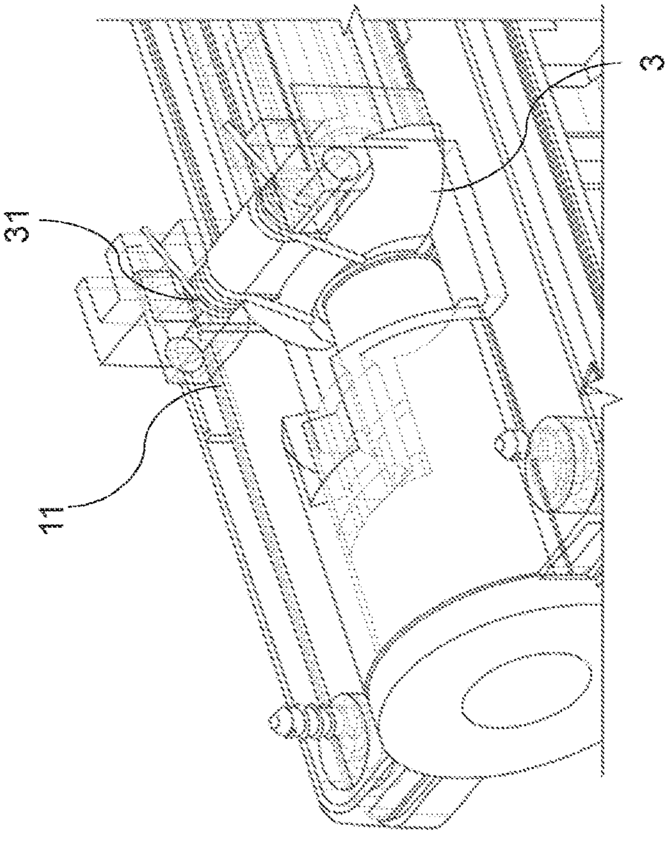

FIG. 1 illustrates a delivery member shield remover assembly arranged with a medicament delivery device (1). The medicament delivery device (1) comprises a housing (11) having a proximal and a distal end. The housing extends along a longitudinal axis (L) and is arranged to receive a medicament container (2) which comprises a delivery member shield (21) therein. The delivery member shield (21) might be a rigid shield or a resilient rubber-like shield or the combination thereof. The delivery member shield remover assembly comprises a delivery member shield remover (3), preferably transversally arranged to the housing (11). The delivery member shield remover (3) further comprises a free end (3*a*) and a fixed end (3*b*) wherein the fixed end is fixedly arranged to the housing (11). In a preferably embodiment as shown in FIG. 1, the delivery member shield remover (3) is hingedly arranged to the housing (11). In another embodiment, the fixed end of the delivery member shield remover is integral with the housing and is configured such that the integral connection between the fixed end of the delivery member shield and the housing comprises resilient/biasing properties. The delivery member shield remover (3) is a body that may have a semi-circular, rectangular, square or trapezoid shape. The delivery member shield remover (3) may further comprises a recess which could be dome shaped or cone shaped arranged on the free end of the delivery member shield remover (3*a*). The recess comprises an edge configured to fit into the gap defined by the delivery member shield (21) and the medicament container (3); such that a contact between the proximal part of the edge of the delivery member shield remover (3) and the distal edge of the delivery member shield (21) is provided. In FIG. 1, it is shown a housing that comprises two housing parts which are connected to each other through a hinge arrangement or said parts can also be integrally having a bendable connection or in alternative embodiment, two housing parts can be completely separated components, and attachable to each other by connection features known in the art such as snap-fit, magnetically fitting or sliding track engagement. The delivery member shield remover (3) is arranged on one of the housing parts and the other housing part is configured to receive the medicament container (2); such that a user is able to place the medicament container (2) laterally into the said housing part, and close the housing (11) by closing the two housing parts together. In an alternative embodiment, the housing (11) can be arranged as a proximal part and a distal part which are removably axially connected to each other and wherein the medicament container (2) can be placed into the housing (11) by a longitudinally insertion/displacement; as shown in FIG. 5 and FIG. 6. After insertion/displacement of the medicament container (2) into the proximal part, the proximal part and the distal part then will be connected to each other.

In an initial position of the delivery member shield remover (3), the delivery member shield remover (3) extends perpendicular to the longitudinal axis (L), or in a preferred embodiment, the delivery member shield remover (3) extends substantially towards the proximal end and forming an angle, e.g. between 0, 10 to 30 degrees with the longitudinal axis (L); such that once the delivery member shield (21) is aligned with the delivery member shield remover (3) and moves the delivery member shield remover (3) extending perpendicular to the longitudinal axis (L), the slight tension force accumulated in the delivery member shield remover (3) makes the delivery member shield remover (3) grip on the delivery member shield (21) tight. The delivery member shield remover (3) is configured with a broader flipping space in the proximal direction than the flipping space in the distal direction; so that the free end (3*a*) is able to be moved further in the proximal direction than to be moved in the distal direction.

Figure 3:
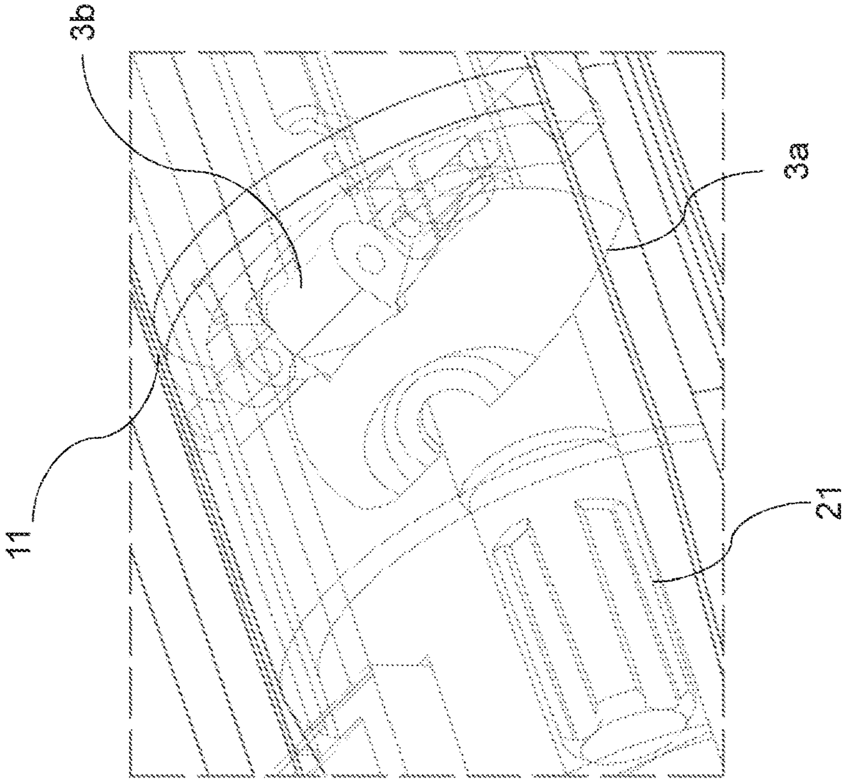
FIGS. 2-3 display the delivery member shield remover assembly of FIG. 1 when the medicament container together with delivery member shield is moved in the proximal direction in relation to the housing such that the free end of the delivery member shield remover interacts with the delivery member shield until the free end of the movable delivery member shield remover contacts the gap defined between the medicament container and the delivery member shield.
Figure 2:
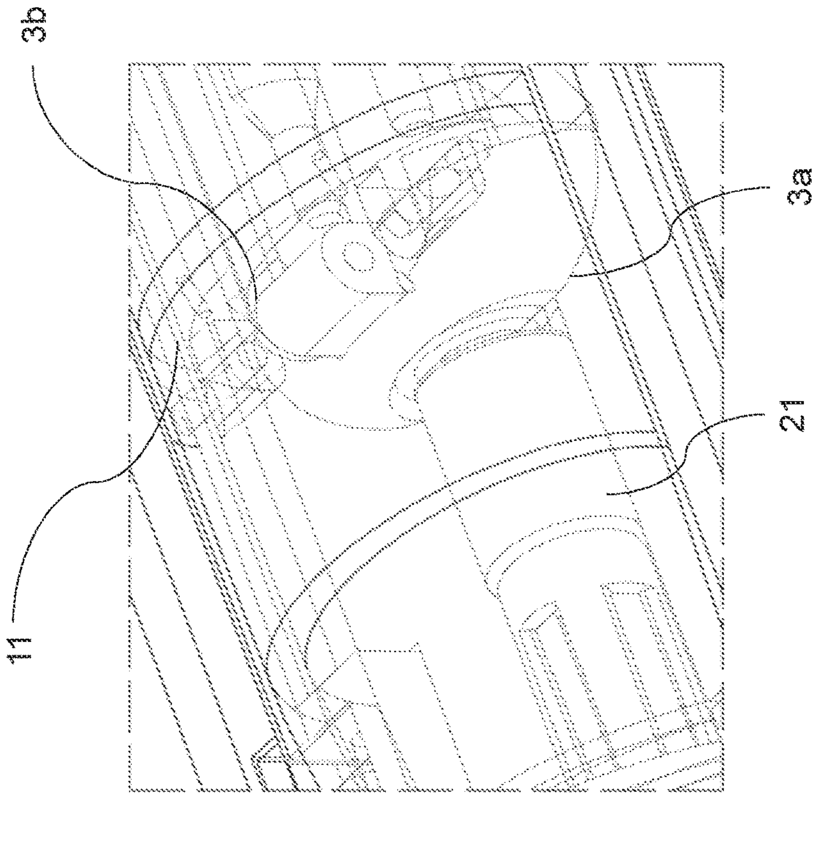

FIG. 2 illustrates part of the device as seen in FIG. 1 wherein the delivery member shield remover (3) is in a ready position in which the free end (3*a*) is positioned in a gap defined by the delivery member shield (21) and the medicament container (2), Since the delivery member shield remover (3) is hingedly or integral and resiliently connected to the housing (11) as seen in FIG. 2, the delivery member shield remover assembly can therefore receive any medicament container (2) having different lengths or size. It also provides the advantage to receive a medicament container, which is not properly placed and aligned with the delivery member shield remover (3). As shown in FIG. 3, if a long medicament container (2) or a misaligned medicament container is received, the delivery member shield remover (3) will then be flipped or pivot by the delivery member shield (21), so that the damage of the remover (3) is prevented. Before initiating the removal of the delivery member shield (21), the position of the medicament container (2) should be adjusted by bidirectional moving the medicament container so that the delivery member shield remover (3) can be moved in the ready position.

For easily bidirectional moving the medicament container (2), the medicament container (2) can be connected to a receiving member such as a container carrier or a gripper or a ledge arm. The receiving member is also connected to a power output source e.g. a motor, a spring or gear wheel; however, if the medicament delivery device is arranged that the user is able to access the medicament container (2), the medicament container (2) can be also moved by the user's hand without any carrier or gripper in between.

Figure 4:
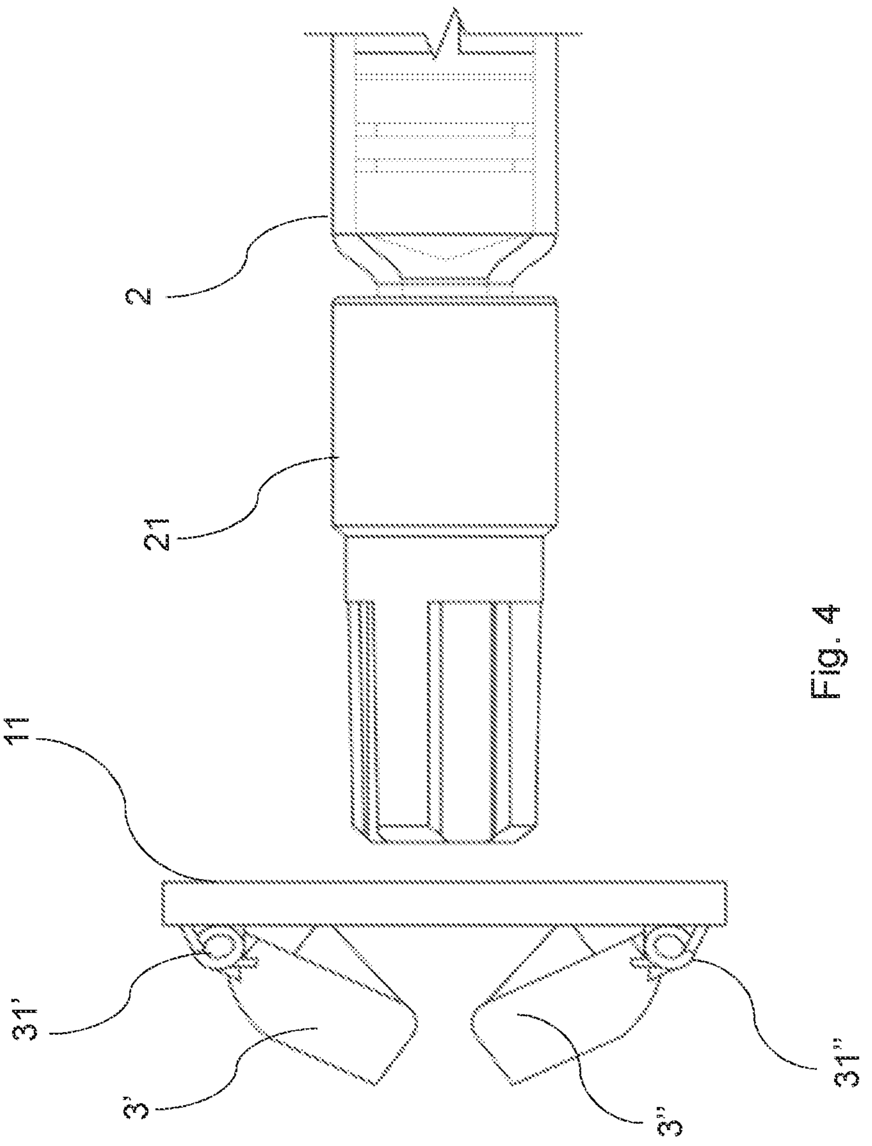
FIGS. 4, 5 and 6 display different embodiments of the delivery member shield remover.

The delivery member shield remover (3) can be arranged as displayed in FIG. 1-3, or alternatively arranged with at least two delivery member shield removers (3', 3") as shown in FIG. 4. Instead of having the delivery member shield remover (3; 3', 3") integral and resiliently connected to the housing, a biasing member such like a spring can be arranged to the delivery member shield remover assembly. It is also possible to obtain the same result with other kind of resilient elements/members known in the art.

The spring might be a torsion spring (31; 31', 31") or a tension spring (31'") arranged between the housing (11) and the fixed end (3*b*) of the delivery member shield remover (3). The biasing member can be located on the hinge between the delivery member shield remover (3) and the housing (11) as shown in FIG. 4-5; or arranged on the hinge at one end and the housing at the housing at the other end (as shown in FIG. 6). The biasing member is arranged to be in a relaxed configuration when the delivery member shield remover is in the initial position. The biasing member can also be an elastic wire or ribbon. The biasing member (31; 31', 31"; 31'") can also be used either with a delivery member shield remover (3; 3', 3") which is integral and resiliently connect to the housing so that the delivery member shield (21) will be easily detached from the medicament container (2). This arrangement might be a preferred solution to use with a design that requires the medicament container (2) to be manually and distally displaced; or it would also be preferred in a design that tends to eject the delivery member shield (21) out of a medicament delivery device so that the user is indicated that the medicament delivery device is ready to be used; especially for those medicament delivery device with that will cover the delivery member by a separate covering member or by the housing of the delivery device after the delivery member shield (21) is detached from the medicament container (2).

FIGS. 1-5 display a delivery member shield remover assembly in which the fixed end of the delivery member shield remover (3; 3', 3") is fixedly connected to the housing (11) of the medicament delivery device (1). FIG. 5 illustrates the delivery member shield remover (3; 3', 3") comprising a biasing member as a torsion spring (31). The torsion spring (31) is arranged to the delivery member shield remover (3; 3', 3") at one end and to the housing (11) at the other end and the coil is received in the hinge between the housing (11) and the delivery member shield remover (3; 3', 3"). The torsion spring is in its relax configuration when the delivery member shield remover (3; 3', 3") is not pivoting; and the torsion spring is configured to accumulate a torque when the delivery member shield remover (3; 3', 3") pivots. When the free end (3*a*) of the delivery member shield remover (3; 3', 3") moves towards the proximal end, the torsion spring (31'") accumulates an anti-clockwise torque; and when the delivery member shield remover (3; 3', 3") moves towards the distal end, the torsion spring accumulates a clockwise torque. Once the clockwise torque accumulated in the torsion spring (31) becomes greater than the friction force between the delivery member shield (21) and the delivery member, the torsion spring will then bias the free end (3*a*) of the delivery member shield remover (3; 3', 3") to move clockwise in relation to the fixed end (3*b*) of the delivery member shield remover (3; 3', 3") such that the delivery member shield (21) is detached from the medicament container (2).

In alternative embodiment as shown in FIG. 6; the delivery member shield remover (3; 3', 3") comprises a biasing member as a tension spring (31'"), which is fixed on the housing at one end and fixed to the delivery member shield remover (3; 3', 3") at the other end; more particularly fixed on an extending part (3*a'*) of the delivery member shield remover (3; 3', 3"). The tension spring is in its relax configuration when the delivery member shield remover (3; 3', 3") is not moved. The tension spring is configured to accumulate an energy with the movement of the delivery member shield remover (3; 3', 3"). The movement between the extending part (3*a'*) and the free end (3*a*) is a seesaw movement. The proximal movement of the free end (3*a*) of the delivery member shield remover (3; 3', 3") causes the tension spring (31'") to be extended and to accumulate a pulling force. The distal movement of the free end (3*a*) of the delivery member shield remover (3; 3', 3") causes the tension spring to be tensioned and to accumulate a pushing force. Once the force accumulated in the tension spring (31'") becomes greater than the friction force between the delivery member shield (21) and the delivery member, the tension spring (31'") will then bias the free end (3*a*) of the delivery member shield remover (3; 3', 3") to move proximally and consequently detach the delivery member shield (21) from the medicament container (2).

In an alternative embodiment, the delivery member shield remover (3; 3', 3") may further be arranged as axial slidable along the longitudinal axis. In this embodiment, the housing (11) comprises a track (12) and the delivery member shield remover (3; 3', 3") comprises a fixed end (3*b'*) acting as a track follower, as shown in FIG. 6. The fixed end (3*b'*) is configured to axially slide along the track (12) but it is rotationally fixed in relation to the housing (11). The movement between the extending part (3*a'*) and the free end (3*a*) when the free end (3*a*) moves proximally is a seesaw movement as described above. The distal movement of the free end (3*a*) of the delivery member shield remover (3; 3', 3") causes the whole delivery member shield remover (3; 3', 3") to slide distally and to tension the tension spring as it is pulled and thereby accumulate a biasing force. Once the pulling force accumulated in the tension spring (31'") becomes greater than the friction force between the delivery member shield (21) and the delivery member; the tension spring (31'") will then bias the free end (3*a*) of the delivery member shield remover (3; 3', 3") to move proximally and thereby detach the delivery member shield (21) from the medicament container (2).

In an alternative embodiment, instead of using a torsion spring or tension spring, the delivery member shield remover (3; 3', 3") can also be associated with a hard stop. The hard stop is arranged on the housing (11), and is configured to abut the movement of the free end (3*a*) of the delivery member shield remover (3; 3', 3") when the free end (3*a*) is moved distally with a predetermined and detach the delivery member shield (21). In this embodiment, the torsion spring or the tension spring is only used for distally placing the free end (3*a*) of the delivery member shield (3; 3', 3").

Figure 7:
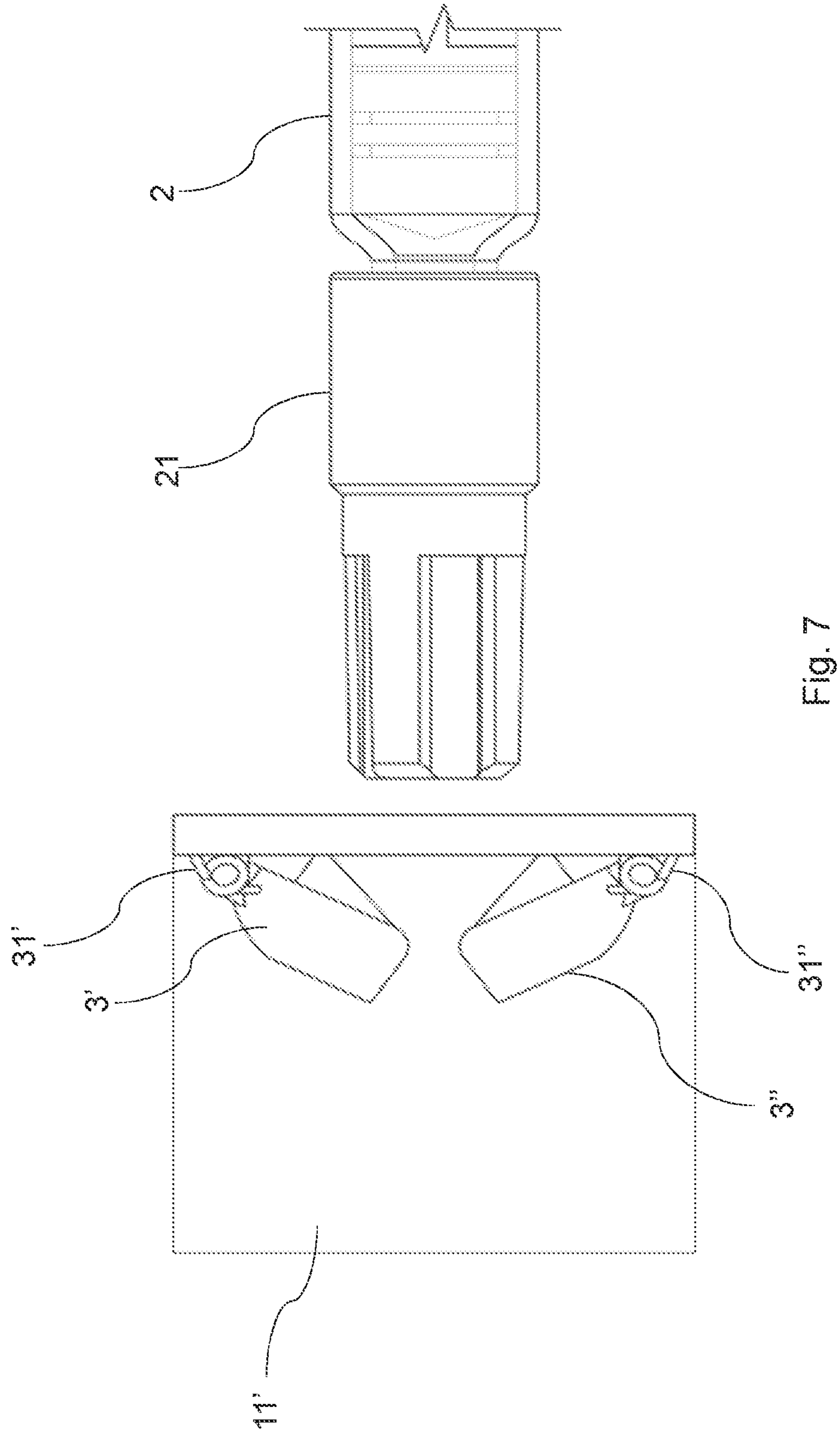
FIG. 7 displays an alternative embodiment of the arrangement of the delivery member shield remover assembly.

Alternatively, the delivery member shield remover (3; 3', 3") is fixedly connected to a housing (11') of a protective cap which is configured to receive the delivery member shield (21) and designed to be removably attached to a medicament delivery device as shown in FIG. 7. The term fixedly refers that the fixed end of the delivery member shield remover is either integral to the housing or hingedly connected though a biasing member. FIG. 7 shows the delivery member shield remover (3; 3', 3") having two removers (3', 3"); however, it is also can be achieved by only using one delivery member shield remover (3) as described in the first embodiment but it is also possible to use a plurality of removers.

Once the medicament container (2) is moved distally in relation to the housing (11, 11'); such like moved under an output force of a motor or a power accumulating member, e.g. spring or gas; or even a manually rotating gear wheel; the free end (3*a*) will then tightly engage with the edge of the delivery member shield (21) and move distally with the delivery member shield (21) and the whole medicament container (2). The delivery member shield remover (3) will then be tensioned until a bias threshold of the delivery member shield remover (3) is reached. The bias threshold is reached when he tensioning force accumulated in the delivery member shield remover (3) is greater than the friction between the delivery member shield (21) and the delivery member of the medicament container (2). The delivery member shield (21) will then be detached from the medicament container (2) and ejected. The delivery member shield remover (3) will move back to the initial position.

The disclosed concept has mainly been described above with reference to a few examples. However, as is readily appreciated by a person skilled in the art, other embodiments than the ones disclosed above are equally possible within the scope of the disclosed concept, as defined by the appended claims.

The invention claimed is:

1. A delivery member shield remover assembly adapted to interact with a delivery member shield which is releasably attached to a movable medicament container; wherein the assembly comprises:

- a housing which extends along a longitudinal axis and which has a proximal and a distal end; and
- a delivery member shield remover having a free end and a fixed end and wherein said delivery member shield remover is resiliently connected to the housing,
- wherein the fixed end is connected to the housing at a resilient connection point and the free end of the delivery member shield remover is configured to be positioned in a gap defined between the medicament container and the delivery member shield such that a distal movement of the movable medicament container in relation to the housing, forces the free end of the delivery member shield remover to move in a distal direction until the delivery member shield remover reaches a bias threshold and forces the delivery member shield to detach from the movable medicament container, wherein the delivery member shield remover will then move back to its initial position via the resilient connection to the housing by rotating the delivery member shield remover around the resilient connection point at its fixed end.

2. The delivery member shield remover assembly according to claim 1, wherein the free end of the delivery member shield remover is movable in the proximal direction when the movable medicament container is moved in the proximal direction in relation to the housing such that the free end of the delivery member shield remover interacts with the delivery member shield until the free end of the movable delivery member shield remover contacts the gap defined between the medicament container and the delivery member shield.

3. The delivery member shield remover assembly according to claim 1, wherein the fixed end of the delivery member shield remover is hingedly connected to the housing.

4. The delivery member shield remover assembly according to claim 1, wherein the delivery member shield remover is integral with the housing.

5. The delivery member shield remover assembly according to claim 1, wherein the delivery member shield remover assembly further comprises a biasing member arranged to connect the movable delivery member shield remover and the housing, and configured to bias the movable delivery member shield remover.

6. The delivery member shield remover assembly according to claim 5, wherein the biasing member is a torsion or a tension spring.

7. The delivery member shield remover assembly according to claim 1, wherein the delivery member shield comprises a resilient shield member or a rigid shield member or a combination thereof.

8. The delivery member shield remover assembly according to claim 1, wherein the distal movement of the movable medicament container is driven by a motor.

9. The delivery member shield remover assembly according to claim 1, the distal movement of the movable medicament container is driven by a power accumulating member.

10. The delivery member shield remover assembly according to claim 1, the distal movement of the movable medicament container is manually driven.

11. The delivery member shield remover assembly according to claim 1 wherein the housing is a protective cap configured to receive the delivery member shield and which is designed to be removably attached to a medicament delivery device.

12. The delivery member shield remover assembly according to claim 1 wherein the housing is defined as being the housing of a medicament delivery device.

13. A method of removing a delivery member shield of a medicament container, comprising:

- providing a housing which extends along a longitudinal axis (L) and which has a proximal and a distal end; and a delivery member shield remover having a free end and a fixed end and wherein said delivery member shield remover is resiliently connected to the housing via the fixed end at a resilient connection point;
- placing the medicament container with the delivery member shield movably related to the delivery member shield remover;
- moving the medicament container bidirectional relatively to the delivery member shield remover until the free end of the delivery member shield remover positions in a gap defined between the medicament container and the delivery member shield;
- moving the medicament container in the distal direction until the delivery member shield remover reaches a bias threshold and forces the delivery member shield to detach from the movable medicament container, wherein the delivery member shield remover will then move back to its initial position via the resilient connection to the housing by rotating the delivery member shield remover around the resilient connection point at its fixed end.

14. The method according to claim 13, wherein the fixed end of the delivery member shield remover is hingedly connected to the housing.

15. The method according to claim 14, wherein the delivery member shield remover is connected to the housing with a biasing member; wherein the biasing member is configured to bias the movable delivery member shield remover.

16. A delivery member shield remover assembly adapted to interact with a delivery member shield which is releasably attached to a movable medicament container, where the assembly comprises:

- a housing which extends along a longitudinal axis and which has a proximal and a distal end; and
- a delivery member shield remover having a free end and a fixed end, where the delivery member shield remover further comprises a biasing member that is connected to the housing and biases the delivery member shield remover,
- wherein the fixed end is hingedly connected to the housing and the free end of the delivery member shield remover is configured to be positioned in a gap defined between the medicament container and the delivery member shield such that a distal movement of the movable medicament container in relation to the housing forces the free end of the delivery member shield remover to move in a distal direction until the delivery member shield remover reaches a bias threshold and forces the delivery member shield to detach from the movable medicament container, and wherein the delivery member shield remover will then move back to its initial position by rotating the delivery member shield remover about the hinged connection via the biasing member.

17. The delivery member shield remover assembly according to claim 16, wherein the biasing member is a torsion or tension spring, and the distal movement of the movable medicament container is driven by a motor.

18. The delivery member shield remover assembly according to claim 16, wherein the housing is a protective cap of a medicament delivery device, where the protective cap is operatively attached to the delivery member shield and is designed to be removably attached to the medicament delivery device.

19. The delivery member shield remover assembly according to claim 16, wherein the delivery member shield comprises a resilient shield member surrounded by a rigid shield member.

20. The delivery member shield remover assembly according to claim 16, the distal movement of the movable medicament container is manually driven.

* * * * *